(12) United States Patent
Dorok et al.

(10) Patent No.: US 9,502,660 B2
(45) Date of Patent: Nov. 22, 2016

(54) ELECTRONIC DEVICE AND COMPOUND

(75) Inventors: Sascha Dorok, Dresden (DE); Ulrich Heggemann, Dresden (DE); Ina Faltin, Dresden (DE); Manuela Klose, Dresden (DE); Rudolf Lessmann, Duesseldorf (DE)

(73) Assignee: NOVALED GMBH, Dresden (DE)

( * ) Notice: Subject to any disclaimer, the term of this patent is extended or adjusted under 35 U.S.C. 154(b) by 41 days.

(21) Appl. No.: 14/126,331

(22) PCT Filed: Jun. 22, 2012

(86) PCT No.: PCT/EP2012/002647
§ 371 (c)(1),
(2), (4) Date: Mar. 17, 2014

(87) PCT Pub. No.: WO2012/175219
PCT Pub. Date: Dec. 27, 2012

(65) Prior Publication Data
US 2014/0182681 A1    Jul. 3, 2014

(30) Foreign Application Priority Data
Jun. 22, 2011 (EP) .................... 11170945

(51) Int. Cl.
| | |
|---|---|
| *B82Y 10/00* | (2011.01) |
| *C07F 9/06* | (2006.01) |
| *C07F 9/535* | (2006.01) |
| *H01L 51/00* | (2006.01) |
| *H01L 51/42* | (2006.01) |

(52) U.S. Cl.
CPC ........... *H01L 51/0059* (2013.01); *B82Y 10/00* (2013.01); *C07F 9/065* (2013.01); *C07F 9/5355* (2013.01); *H01L 51/005* (2013.01); *H01L 51/0046* (2013.01); *H01L 51/4253* (2013.01); *Y02E 10/549* (2013.01)

(58) Field of Classification Search
CPC ...... B82Y 10/00; C07F 9/065; C07F 9/5355; H01L 51/005; H01L 51/0059; H01L 51/0046; H01L 51/4253; Y02E 10/549
See application file for complete search history.

(56) References Cited

U.S. PATENT DOCUMENTS

| | | |
|---|---|---|
| 3,188,294 A | 6/1965 | Maier |
| 8,258,501 B2 | 9/2012 | Werner et al. |
| 8,431,046 B2 | 4/2013 | Zeika et al. |
| 2007/0090371 A1 | 4/2007 | Drechsel et al. |
| 2007/0145355 A1 | 6/2007 | Werner et al. |
| 2008/0145520 A1* | 6/2008 | Yumoto .......................... 427/66 |

OTHER PUBLICATIONS

CAS No. 86133-53-1, entered in STN Nov. 16, 1984.*
CAS No. 51640-69-8, entered in STN Nov. 16, 1984.*
CAS No. 66949-27-7, Entered in STN Nov. 16, 1984, pp. 1.*
CAS No. 207617-64-9, Entered in STN Jun. 25, 1998, pp. 1.*
Ameri et al., "Organic Tandem Solar Cells: A Review," Energy Environ. Sci., 2009, 2:347-363.
Bard et al., "Electrochemical Methods: Fundamentals and Applications," Wiley, 2000, 2nd Edition, p. 239-247.
Escobar et al., "Electron-Donating Properties of p-Phenylene Phosphine Imides: An Electrochemical and Spectroscopic Investigation," Org. Lett., 2002, 4(13):2213-2216.
Guidi et al., "Bis(phosphine Imide)s: Easily Tunable Organic Electron Donors," J. Org. Chem., 2005, 70:7737-7743.
Hong et al., "Antenna Effects and Improved Efficiency in Multiple Heterojunction Photovoltaic Cells Based on Pentacene, Zinc Phthalocyanine, and C60," American Institute of Physics, 2009, 106:064511-1-6.

(Continued)

*Primary Examiner* — Paul A Zucker
*Assistant Examiner* — Mark Luderer
(74) *Attorney, Agent, or Firm* — Sutherland Asbill & Brennan LLP

(57) ABSTRACT

The present invention relates to an electronic device comprising a compound according to formula 1 A-B (1) and wherein —$Ar^1$ is a C6-C18 arylene, which can be monocyclic or polycyclic and may be optionally substituted by one or more $C_1$-$C_{10}$-alkyl or $C_3$-$C_{10}$-cycloalkyl groups, —$Ar^2$ is a C6-C18 arene skeleton, optionally substituted with electron donating groups $R^4$, —$B^1$ and $B^2$ are independently selected from B and $Ar^2$, —$B^3$ is independently selected from the same group as B, —$R^1$, $R^2$, $R^3$ are independently selected from alkyl, arylalkyl, cycloalkyl, aryl, dialkylamino, - x is selected from 0, 1, 2 and 3, wherein for x>1 each $Ar^1$ may be different, - y is a non-zero integer up to the overall count of valence sites on the arene skeleton, - z is a integer from zero up to the overall count of valence sites on the arene skeleton minus y; as well as a respective compound according to formula A-B.

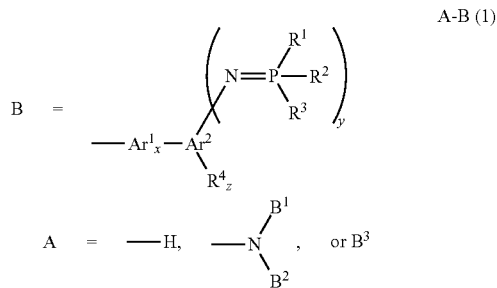

18 Claims, 2 Drawing Sheets

(56) References Cited

OTHER PUBLICATIONS

Horner et al., "Phosphinimino-Verbindungen Aus Phosphindihalogeniden und Primaren Aminen," Liebigs Annalen der Chemie, 1959, 627:132-162.

Liao et al., "Highly Efficient Inverted Polymer Solar Cell by Low Temperature Annealing of CS2CO3 Interlayer," Applied Physics Letters, 2008, 92:173303-1-3.

Matni et al., "ESR/DFT Study of Bis-iminophosphorane Cation Radicals," Magn. Reson. Chem., 2007, 45:1011-1017.

Matni et al., "Oxidation Products of Iminosphosphorane and Bis-Iminophosphorane: An EPR Study," Chemical Physics Letters, 2005, 411:23-27.

PCT International Search Report for PCT/EP2012/002647 mailed Oct. 22, 2012.

Pomerantz et al., "NMR Spectroscopy and Cyclic Voltammetry of N-Aryl-P,P,P-triphenylphospha-$\lambda\lambda5$-azenes. Substituent Effects and Correlation with Molecular Orbital Calculations," J. Org. Chem., 1986, 51:1223-1230.

Second Chinese Office Action for CN Application No. 201280031104.8 mailed Apr. 20, 2016 (17 pages).

* cited by examiner

ELECTRONIC DEVICE AND COMPOUND

The invention relates to an electronic device and a compound.

BACKGROUND OF THE INVENTION

Organic solar cells (OSCs), also known as organic photovoltaic (OPV) devices, have the most different device architectures. Typically, they comprise at least one organic semiconducting layer that is arranged between two electrodes. The organic layer can be a blend of a donor and an acceptor such as P3HT (poly3-hexyl-tiophene) and PCBM (phenyl C61 Butyric Acid Methyl Ester). Such simple device structures only achieve reasonably efficiencies if interfacial injection layers are used to facilitate charge carrier injection/extraction (Liao et al., Appl. Phys. Lett., 2008.92: p. 173303). Other organic solar cells have multi-layer structures, sometimes even hybrid polymer and small molecule structures. Also tandem or multi-unit stacks are known (see US 2007/090371 A1, or Ameri, et al., Energy & Env. Science, 2009.2: p. 347). Multi-layer devices can be easier optimized since different layers can comprise different chemical compounds (or simply compounds) and their mixtures which are suitable for different functions. Typical functional layers are transport layers, photoactive layers, injection layers, etc.

Optically active compounds are compounds with a high absorption coefficient, for at least a certain wavelength range of the solar spectra, which compounds convert absorbed photons into excitons which excitons in turn contribute to the photocurrent. The photoactive compounds are typically used in a donor-acceptor heterojunction, where at least one of the donor or the acceptor is the light absorbing compound. The interface of the donor-acceptor heterojunction is responsible for separating the generated excitons into charge carriers. The heterojunction can be a bulk-heterojunction (a blend), or a flat (also called planar) heterojunction, additional layers can also be provided (Hong et al, J. Appl. Phys., 2009.106: p. 064511).

The loss by recombination must be minimized for high efficiency OPV devices. Therefore, the compounds in the heterojunction must have high charge carrier mobilities and high exciton diffusion lengths. The excitons have to be separated into charge carriers at the heterointerface and the charge carriers have to leave the optically active region before any recombination takes place. For that reasons, currently, fullerenes (C60, C70, PCBM, and so on) are the preferred choice as acceptor materials in OPV devices.

Transport compounds for opto-electronic devices are required to be transparent, at least in the wavelengths wherein the device is active, and have good semiconducting properties. These semiconducting properties are intrinsic, such as energy levels or mobility, or extrinsic, such as charge carrier density. The charge carrier density can also be extrinsically influenced by doping the compound with an electrical dopant.

OSCs very often require the use of at least one n-dopant in an n-doped electron transport layer, or as a pure interlayer promoting electron injection from a conductive layer into a semiconductor or from a semiconductor into another semiconductor.

Several different n-dopants are known, such as Tetrakis (1,3,4,6,7,8-Hexahydro-2H-pyrimido [1,2-a]pyrimidinato) ditungsten (II) from EP 1 768 200 B1, Bis(2,2'-terpyridin) ruthenium, and others. One main problem of n-dopants is that since they are strong donors, they easily degrade by reacting with atmospheric oxygen. There are not many known compounds which are able to directly work as n-dopants which are also air stable. Precursor-compounds were developed with the aim to provide air stable organic compounds and being able to work as n-dopants, examples of such precursors are disclosed in WO 2007/107306 A1.

Also, only a few organic compounds are known to be able to efficiently dope low LUMO compounds used in OSCs, such as fullerenes (e.g. C60) or fullerene derivatives (e.g. PCBM), for example the compounds disclosed in US 2007/145355 A1.

SUMMARY OF THE INVENTION

It is the object of the invention to provide improved technologies for an electronic device. Other objectives are to provide high conductivities and thermal stabilities of doped layers in electronic devices, and also to provide a compound with an easy processability.

According to one aspect of the invention an electronic device comprising a compound according to formula 1

$$A\text{-}B \tag{1},$$

wherein

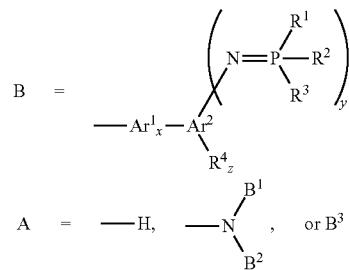

and wherein

Ar$^1$ is a C6-C18 arylene, which can be monocyclic or polycyclic and may be optionally substituted by one or more C$_1$-C$_{10}$-alkyl or C$_3$-C$_{10}$-cycloalkyl groups, Ar$^2$ is a C6-C 18 arene skeleton, optionally substituted with electron donating groups R$^4$, B$^1$ and B$^2$ are independently selected from B and Ar$^2$, B$^3$ is independently selected from the same group as B R$^1$, R$^2$, R$^3$ are independently selected from alkyl, arylalkyl, cycloalkyl, aryl, dialkylamino, x is selected from 0, 1, 2 and 3, wherein for x>1 each Ar$^1$ may be different, y is a non-zero integer up to the overall count of valence sites on the arene skeleton, z is an integer from zero up to the overall count of valence sites on the arene skeleton minus y.

Preferably,

Ar$^2$ is a benzene or naphthalene skeleton,

R$^4$ is selected from alkyl and alkoxy,

R$^1$, R$^2$, R$^3$ are independently selected from alkyl, arylalkyl, cycloalkyl, aryl, dialkylamino, x=0 or Ar$^1$=phenylene, y is selected from 1, 2, 3 and 4 if Ar$_2$ is benzene$_2$ or from 1, 2, 3, 4, 5 and 6 if Ar$^2$ is naphthalene, z is selected from 0 and 1 if Ar$^2$ is benzene or from 0, 1 and 2 if Ar$^2$ is naphthalene.

According to another preferred aspect of the invention, in the compound according to the Formula 1

Ar$^2$ is a benzene skeleton

R$^4$ is selected from alkyl and alkoxy, $R^1$, $R^2$, $R^3$ are independently selected from alkyl, arylalkyl, cycloalkyl, aryl, dialkylamino, x=0 or $Ar^1$=1,4-phenylene, y is selected from 1, 2, 3 and 4.

According to yet other preferred embodiments of the invention, in the compound according to Formula 1, $R^4$ is selected from alkyl and alkoxy, $R^1$, $R^2$, $R^3$ are independently selected from alkyl, arylalkyl, cycloalkyl, aryl, dialkylamino, x=0

A=H, y=1 or 2, z=1 or

A=$B^3$ and the sum of all y is at least 3.

The components $R^1$-$R^4$ and the superscripts x, y and z of the compound according to Formula 1 can be selected independently from each other for each B. Also in the case that A equals B leading to a compound B—$B^3$, the B and $B^3$ can be different. The component A of the compound according to Formula 1 can be arranged in para position, ortho position or meta position at any of the phenyl rings.

In any of the above mentioned embodiments of the invention, preferably, $R^1$-$R^3$ is straight or branched, saturated or unsaturated C1-C24 alkyl, saturated or unsaturated C3-C24 cycloalkyl or alkyl comprising at least one cyclic structure, wherein up to four ether linkages can be included within any of the above mentioned alkyl or cycloalkyl structure with a provision that oxygen atoms are in any case separated by at least two carbon atoms, C6-C24 aryl, wherein the overall count of carbon atoms includes also any possible substitution by a single substituent or more substituents selected from saturated or unsaturated, straight or branched alkyl or cycloalkyl, aryl, arylalkyl or alkylaryl groups and within this substitution up to three alkyl groups can be attached to the arene core by an ether linkage or up to six alkyl groups can be attached through a disubstituted nitrogen atom, C7-C25 arylalkyl, wherein the overall C atom count includes also a possible substitution on the arene ring or rings and within this substitution up to three alkyl groups can be attached to the arene ring or rings through an ether linkage or up to six alkyl groups through a disubstituted nitrogen atom, C2-C24 dialkylamino, wherein the alkyl groups may be the same or different, straight or branched, may include also alicyclic or aromatic structures or be unsaturated with a provision that the carbon atom bearing a double or triple bond is not adjacent to nitrogen. The two alkyls in the dialkylamino group may be so linked that they form a cycle comprising the nitrogen atom. Up to four ether linkages can be included between methylene groups of the dialkylamino group, with a provision that in any case the nitrogen and/or oxygen atoms are separated by at least two carbon atoms. Two $R^1$-$R^3$ groups may be linked so that they form a cyclic structure including the phosphorus atom. More preferably, $R^1$-$R^3$ is a C1-C4 alkyl, C3-C10 cycloalkyl, C7-C10 arylalkyl, C6-C14 aryl, C2-C12 dialkylamino. Particularly preferably, each of $R^1$-$R^3$ is independently selected from methyl, isopropyl, tert.-butyl, cyclohexyl, phenyl, tolyl, xylyl, mesityl, naphthyl, anthryl, phenanthryl, 1,1'-biphenyl-yl, 1,3-diisopropylphenyl, benzyl, 4-methoxybenzyl, dimethylamino. Most preferably, $R^1$-$R^3$ is 1,3-dimethylphenyl.

If $R^4$ is alkyl or alkoxy, then the alkyl group can be straight or branched, saturated or unsaturated. That alkyl can also include a cyclic structure, saturated or unsaturated. If more than one $R^4$ occur on the same arene skeleton, then they also can form together a cyclic structure. Preferably, if $R^4$ is alkyl or alkoxy, its overall count of carbon atoms is in the range C1-C22. More preferably, $R^4$ is selected from methyl, methoxy, ethyl, ethoxy, propyl, propoxy, isopropyl, isopropoxy, butyl, butoxy, tert-butyl, tert.-butoxy, cyclohexyl, benzyl, benzyloxy.

In a preferred embodiment, the electronic device is an organic electronic device.

According to a preferred embodiment of the invention, the compound according to Formula 1 is used as an n-dopant.

According to a preferred embodiment, the electronic device has a layered structure comprising several layers, wherein at least one of the layers comprises the compound of Formula 1. The electronic device may further comprise an electron transport layer. Alternatively or supplementary, the electronic device may comprise a first electrode and/or a second electrode.

In a preferred embodiment, the layer of the electronic device comprising the compound of Formula 1 is an electron transport layer. More preferably, the electronic device comprises an electron transport layer which comprises an electron transport compound and the compound according to Formula 1 forming a homogeneous mixture. According to a another preferred mode of the invention, the layer of the electronic device comprising the compound of Formula 1 is in direct contact to an electron transport layer. In a preferred mode of the invention, the electron transport layer comprises a fullerene or a fullerene derivative as its main component.

If used as an electron extracting layer, the layer of the electronic device comprising the compound of Formula 1 has preferably a thickness of less than 5 nm.

Preferably, the layer of the electronic device comprising the compound of Formula 1 is in direct contact to an electrode, more preferably a cathode. In addition or alternatively, the layer comprising the compound according to Formula 1 is arranged between the electron transport layer and the cathode.

In one aspect of the invention, the electronic device comprises a connecting unit. In a preferred embodiment, the layer of the electronic device comprising the compound of Formula 1 is part of the connecting unit.

In a preferred mode of the invention, the electronic device is a solar cell, preferably an organic solar cell (OSC). The solar cell can comprise, for example, an anode, a cathode and a light absorbing layer. In a preferred embodiment, the organic solar cell further comprises the compound according to Formula 1, wherein the compound is comprised between the light absorbing layer and the cathode. In a preferred aspect of the invention, the organic solar cell comprises a pi, ni, or pin structure, comprising a first p, i, or n layer each. Here, p denotes a p-doped hole transport layer, n denotes a n-doped electron transport layer, and i is an intrinsic photoactive layer (see US 2007/090371 A1 for further details). The transport layers have a greater HOMO-LUMO gap than the photoactive layer (HOMO—highest occupied molecular orbital, LUMO—lowest unoccupied molecular orbital).

The solar cell can preferentially comprise a light absorbing unit comprising the light absorbing layer and an additional light absorbing unit comprising an additional light absorbing layer. The connecting unit can be a pn-junction connecting the light absorbing unit to the additional light absorbing unit. Preferably, the connecting unit is a pn-junction connecting the light absorbing unit to the additional light absorbing unit in a tandem device or in a multiple stacked device. Multiple stacked devices are devices with three or more light absorbing units, sometimes also called multi tandem. Multiple stacked pin, pi, or ni devices are preferred. In addition or in alternative, the connecting unit can be a pn-junction connecting the cathode or the anode to the light absorbing unit.

The invention has the advantages that high conductivity can be achieved by doping typical electron transport materials (ETM) used for OSCs. With the use of the compound according to Formula 1, it is possible to obtain conductivities on the order of 1 S/cm with a doping concentration of 10 mol. %, which is a high value for organic systems. Furthermore, the compound according to Formula 1 has a high stability allowing it to be processed, for example, in vacuum, e.g. by vacuum thermal evaporation (VTE), or by organic vapor phase deposition (OVPD). Alternatively, the compound according to Formula 1 can be processed by solution processing under inert atmosphere or even exposed to air.

In a preferred embodiment, the compound according to Formula 1 is inserted in a matrix material forming a doped layer. Herewith, cations derived from the molecules of the compound according to Formula 1 are formed, in particular by the transfer of at least one electron from the compound according to Formula 1 to the surrounding matrix material. In the process, anions of the matrix material are also formed. In this way, the matrix material obtains a conductivity which is increased in comparison to the conductivity of the undoped matrix material.

The conductivity of an undoped matrix material is generally approximately $10^{-8}$ S/cm, in particular often around $10^{-10}$ S/cm. The matrix material should have a sufficiently high purity. Such purity can be achieved using conventional methods, for example gradient sublimation.

By doping, the conductivity of the matrix material can be increased to more than $10^{-6}$ S/cm. This applies in particular to a matrix material which has a reduction potential of less than −0.3 V vs. Fc/Fc$^+$, preferably less than −0.8 V vs. Fc/Fc$^+$. The notation Fc/Fc$^+$ relates to the redox pair ferrocene/ferrocenium, which is used as reference in an electrochemical potential determination, for example by cyclic voltammetry. Details of cyclovoltammetry and other methods to determine reduction potentials and the relation of the ferrocene/ferrocenium reference couple to various reference electrodes can be found in A. J. Bard et al., "Electrochemical Methods: Fundamentals and Applications", Wiley, 2. Edition, 2000. For typical electron transport materials in OSC, the reduction potential is around −0.8 V vs. Fc/Fc+.

In the present application, a dopant is to be understood as a material which is mixed in a matrix material ("the matrix material is doped with the dopant"). It is also common in the state of the art to use the term "electrical dopant", or just "n-dopant" for the dopant for an ETM.

The layer of the electronic device comprising the compound of Formula 1 arranged adjacent to the electron transport layer can be used in an OSC as an electron extracting layer. It was found that the compound according to Formula 1 can be used as an electron injection layer in an electronic component, preferably between an electrode and a semiconductor layer which may be doped. Alternatively or supplementary, the compound according to Formula 1 can be used as a blocking layer, preferably between an absorbing layer and a transport layer, or as a semiconductor layer in electronic components.

In one preferred aspect of the invention, all organic layers of the electronic device are constituted from small molecules. Preferentially, the small molecules can be deposited by VTE (vacuum thermal evaporation).

In another aspect of the invention, at least one organic semiconducting layer comprises a polymer, wherein the polymer layer and/or at least one additional semiconducting layer comprise a compound according to Formula 1.

The compounds according to Formula 1 have a special advantage of forming very stable n-doped layers with a relatively high conductivity.

The synthesis of the compound according to Formula 1 is known from the literature, see for instance, Horner and Oediger, "*Phosphororganische Verbindungen, XVIII: Phosphinimino-Verbindungen aus Phosphindihalogeniden und Primären Aminen*", Liebigs Annalen der Chemie 1959, v. 627, pp. 132-162.

DESCRIPTION OF EXEMPLARY EMBODIMENTS

In the following, exemplary embodiments are disclosed with reference to figures of a drawing. The figures show:

Figure 1:
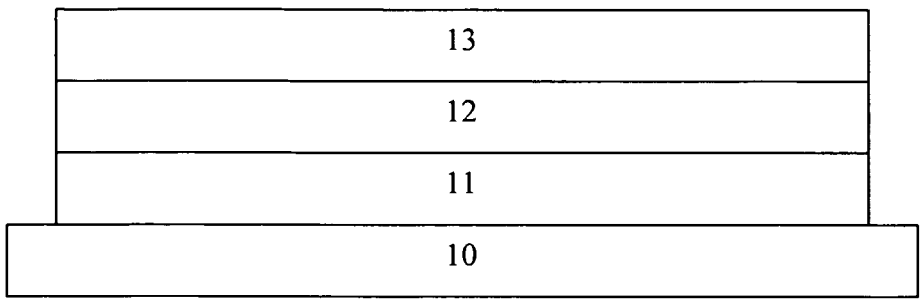
FIG. 1 is a schematic diagram representing a stack of layers which forms a solar cell.

According to FIG. 1, an organic solar cell comprises at least a substrate 10, an anode 11, a light absorbing unit 12, and a cathode 13. The stack of layers can also be inverted, wherein layer 11 would be the cathode, and layer 13 would be the anode. Additional light absorbing units can be provided in the organic solar cell.

In one embodiment, the substrate 10 can be a transparent substrate, such as a glass, or polymeric plate or web. The anode 11 can be a transparent conducting oxide, such as ITO, FTO, AlZO. The cathode 13 can comprise aluminum or an aluminum alloy. At least one light absorbing unit 12 can comprise a blend of a thiophene containing a polymer and a compound according to Formula 1. Alternatively, the light absorbing unit 12 can comprise a blend of a donor polymer, preferentially a thiophene containing a polymer, and an acceptor, preferentially a fullerene or a soluble fullerene derivative. In this embodiment, a layer comprising the compound according to Formula 1 (such as a doped electron transport layer) or consisting of it (such as an electron extracting layer) is formed between the light absorbing unit 12 and the cathode 13. Optionally, the layer structure can be inverted.

In an alternative embodiment, the anode 11 is not transparent and mainly comprises aluminum or an aluminum alloy. The substrate 10 is not necessarily transparent. The cathode 13 comprises a transparent conducting oxide layer or a thin transparent metal layer having a thickness of less than 30 nm.

Still in connection to FIG. 1, in another embodiment, the substrate 10, the anode 11, and the cathode 13 are transparent. In this embodiment, the overall device is semi-transparent, because it does not have 100% absorption of the incident light for any wavelength in the visible range of wavelengths.

Multiple stacked devices (e.g. tandem devices) can also be provided. In such devices, at least one additional light absorbing unit is formed between the light absorbing unit 12 and the cathode 13. Additional organic or inorganic layers may be formed to provide a suitable electronic connection and optical optimization of the layer position. Preferentially, at least parts of these functions are provided by layers comprising a compound according to the Formula 1.

Figure 2:
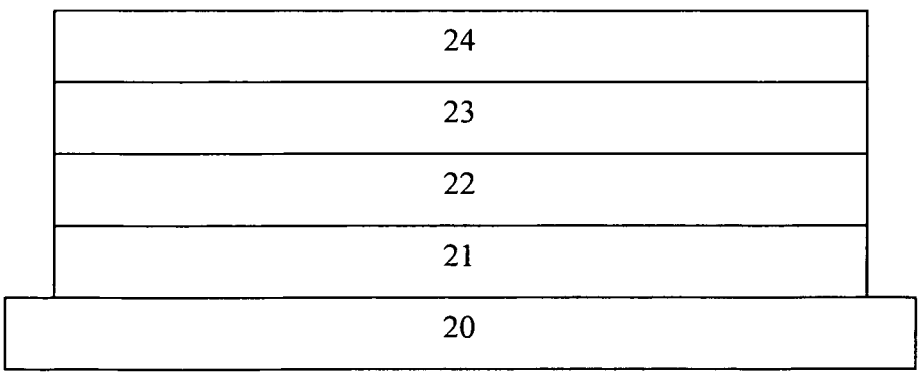
FIG. 2 is a schematic diagram representing a stack of layers of a solar cell comprising an electron transport layer (ETL).

FIG. 2 shows a stack of layers representing an organic solar cell comprising a substrate 20, an anode 21, a light absorbing unit 22 comprising an absorption layer, an organic electron transport layer (ETL) 23, and a cathode 24. The stack of layers can also be inverted. The ETL can be formed between the cathode 24 and the absorption layer 22. Additional light absorbing units can be provided in the solar cell.

In one embodiment, the organic electron transport layer 23 can comprise as its main component an electron transport material (ETM) as a matrix material and the compound according to the Formula 1 as a dopant. The ETL 23 can have any thickness. Its thickness is preferably smaller than 40 nm in the case that there is no additional absorption layer between the light absorbing layer 22 and the cathode 24.

All embodiments as described in connection to FIG. 1 can also be applied for the solar cell according to FIG. 2.

All figures are schematic representations of the layered structure of a solar cell. Some device features are not shown such as electrical connections, encapsulation, optical structures which are external to the electrodes, etc. The layer thicknesses are not drawn to scale. At least one of the electrodes (anode and/or cathode) is transparent in the wavelength range in which the device is active.

In another embodiment, the light absorbing unit 22 is a donor-acceptor bulk heterojunction, e.g. a blend of donor-acceptor materials. The donor is preferentially formed by a strong absorbing compound comprising a pyrrole or a thiophene group. The acceptor is preferentially a $C_{58}$, $C_{60}$, or $C_{70}$ fullerene or a soluble fullerene derivative. The ETL 23 can comprise a compound according to the Formula 1 as a dopant.

In still another embodiment, the light absorbing unit 22 is a donor-acceptor bulk heterojunction e.g. a blend of donor-acceptor materials. The donor is preferentially formed by a strong absorbing compound comprising a pyrrole or a thiophene group. The acceptor can be a compound according to Formula 1.

In the following table, preferred exemplary compounds according to Formula 1 are listed.

| compound | number |
|---|---|
| 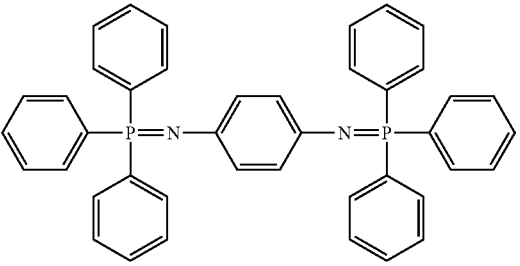 [SMILES: c1ccc(P(=Nc2ccc(N=P(c3ccccc3)(c3ccccc3)c3ccccc3)cc2)(c2ccccc2)c2ccccc2)cc1] | 1 |
| 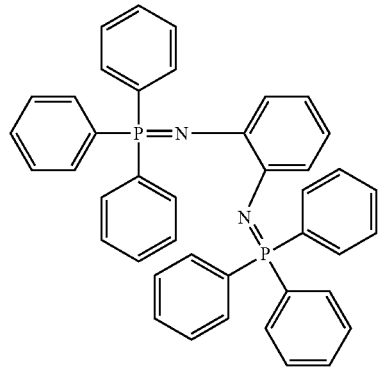 [SMILES: c1ccc(P(=Nc2ccccc2N=P(c2ccccc2)(c2ccccc2)c2ccccc2)(c2ccccc2)c2ccccc2)cc1] | 2 |
| 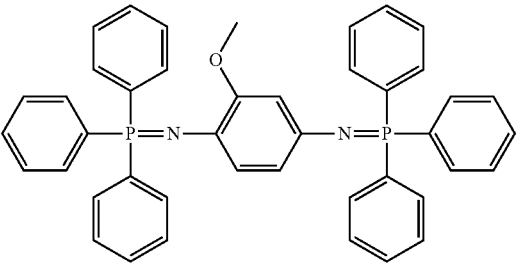 [SMILES: COc1cc(N=P(c2ccccc2)(c2ccccc2)c2ccccc2)ccc1N=P(c1ccccc1)(c1ccccc1)c1ccccc1] | 3 |

| compound | number |
|---|---|
| (structure) | 4 |
| (structure) | 5 |
| (structure) | 6 |
| (structure) | 7 |

| compound | number |
|---|---|
| (structure) | 8 |
| (structure) | 9 |

| compound | number |
|---|---|
| (structure) | 10 |
| (structure) | 11 |
| (structure) | 12 |

-continued
| compound | number |
|---|---|
| 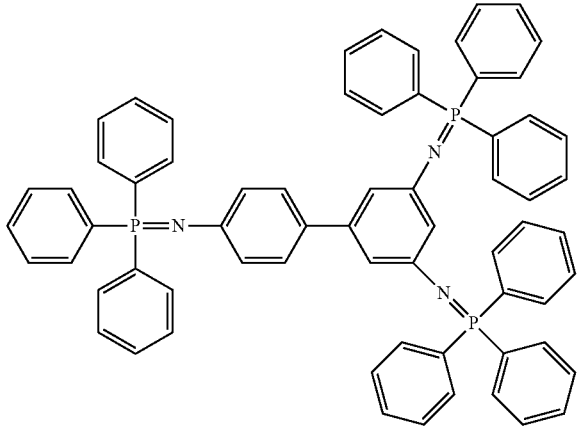 [SMILES: c1ccc(P(=Nc2ccc(-c3cc(N=P(c4ccccc4)(c4ccccc4)c4ccccc4)cc(N=P(c4ccccc4)(c4ccccc4)c4ccccc4)c3)cc2)(c2ccccc2)c2ccccc2)cc1] | 13 |
| 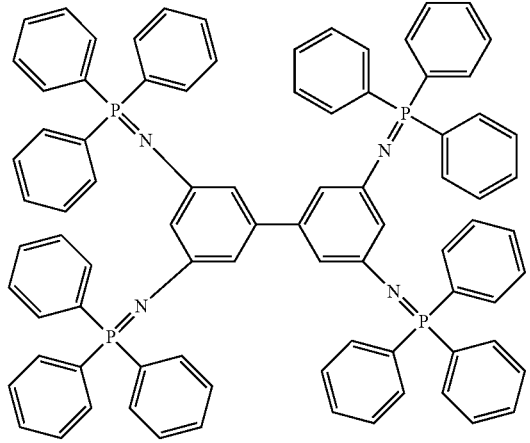 [SMILES: c1ccc(P(=Nc2cc(N=P(c3ccccc3)(c3ccccc3)c3ccccc3)cc(-c3cc(N=P(c4ccccc4)(c4ccccc4)c4ccccc4)cc(N=P(c4ccccc4)(c4ccccc4)c4ccccc4)c3)c2)(c2ccccc2)c2ccccc2)cc1] | 14 |
| 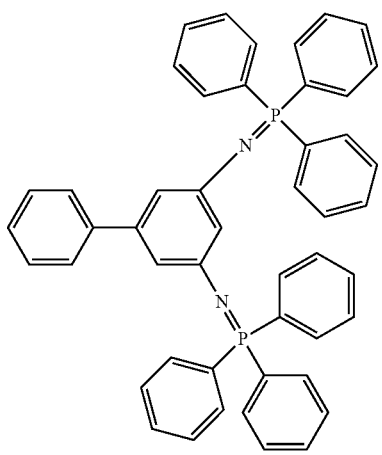 [SMILES: c1ccc(-c2cc(N=P(c3ccccc3)(c3ccccc3)c3ccccc3)cc(N=P(c3ccccc3)(c3ccccc3)c3ccccc3)c2)cc1] | 15 |

-continued

| compound | number |
|---|---|
| | 16 |
| | 17 |
| | 18 |

-continued
| compound | number |
|---|---|
| 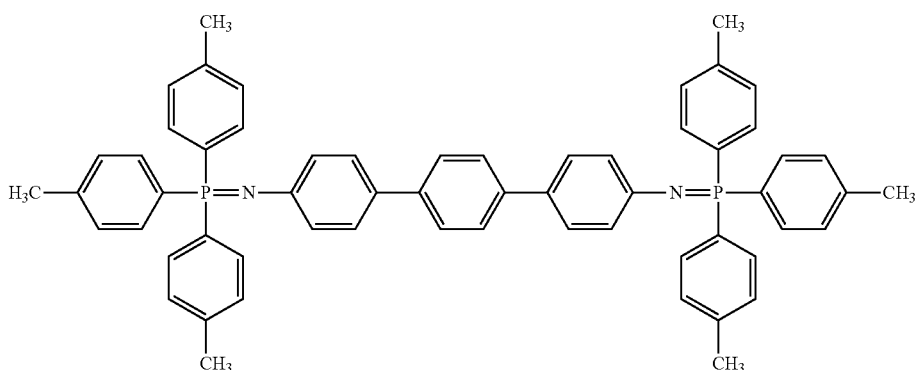 | 19 |
| 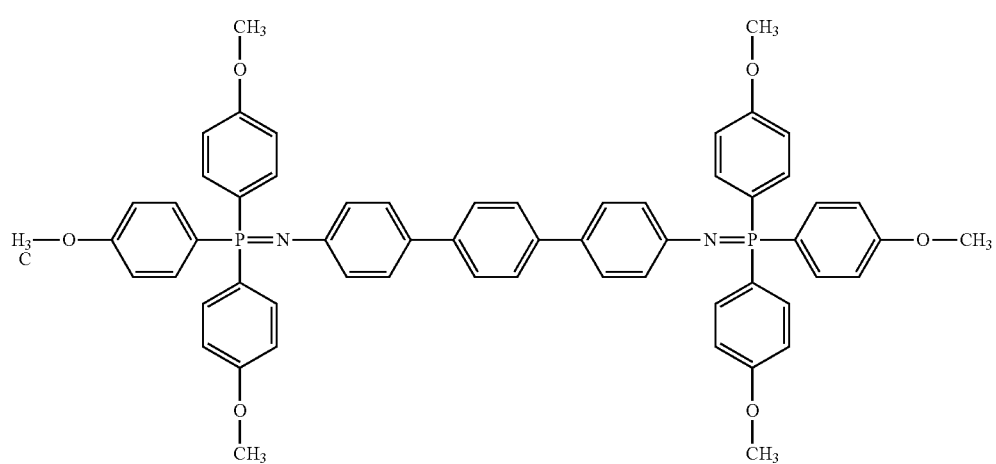 | 20 |
| 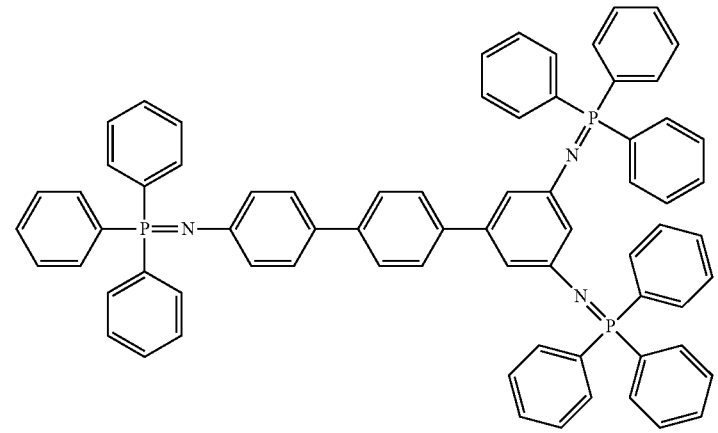 [SMILES: c1ccc(P(=Nc2ccc(-c3ccc(-c4cc(N=P(c5ccccc5)(c5ccccc5)c5ccccc5)cc(N=P(c5ccccc5)(c5ccccc5)c5ccccc5)c4)cc3)cc2)(c2ccccc2)c2ccccc2)cc1] | 21 |

| compound | number |
|---|---|
| 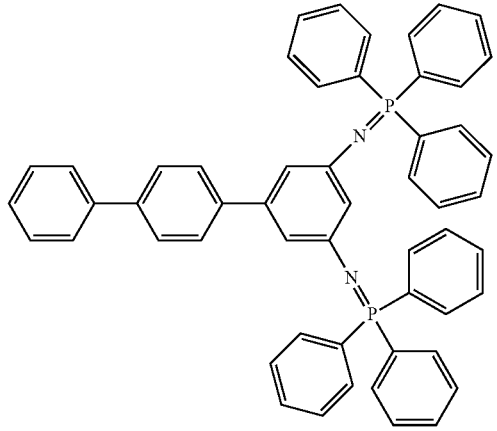 [SMILES: c1ccc(-c2ccc(-c3cc(N=P(c4ccccc4)(c4ccccc4)c4ccccc4)cc(N=P(c4ccccc4)(c4ccccc4)c4ccccc4)c3)cc2)cc1] | 22 |
| 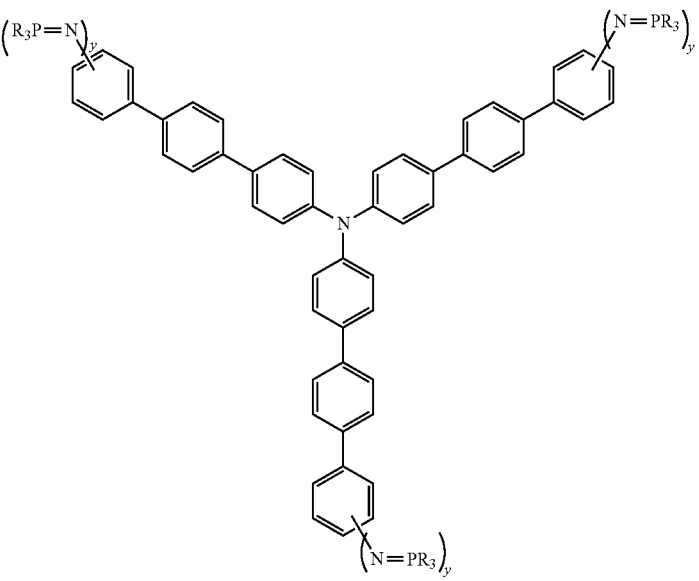
R = Phenyl | 23 |
| 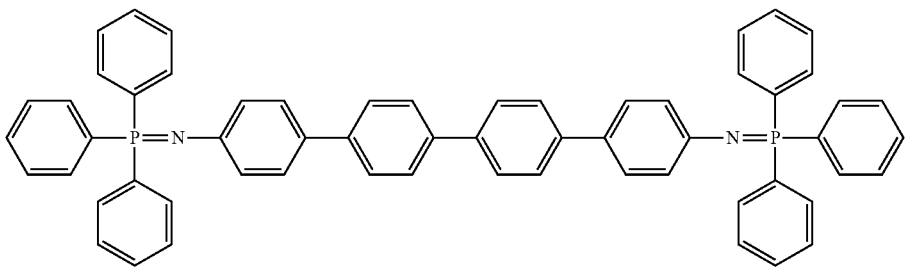 [SMILES: c1ccc(P(=Nc2ccc(-c3ccc(-c4ccc(-c5ccc(N=P(c6ccccc6)(c6ccccc6)c6ccccc6)cc5)cc4)cc3)cc2)(c2ccccc2)c2ccccc2)cc1] | 24 |

-continued
| compound | number |
|---|---|
| 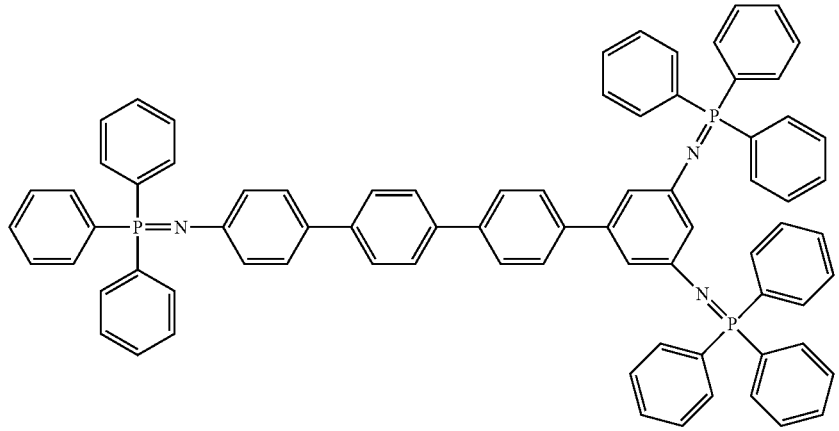 [SMILES: c1ccc(P(=Nc2ccc(-c3ccc(-c4ccc(-c5cc(N=P(c6ccccc6)(c6ccccc6)c6ccccc6)cc(N=P(c6ccccc6)(c6ccccc6)c6ccccc6)c5)cc4)cc3)cc2)(c2ccccc2)c2ccccc2)cc1] | 25 |
| 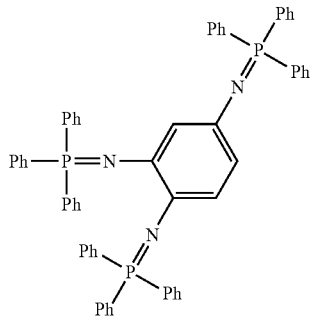
Ph = phenyl | 26 |
| 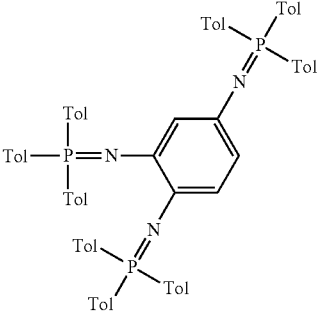
Tol = p-Tolyl | 27 |
| 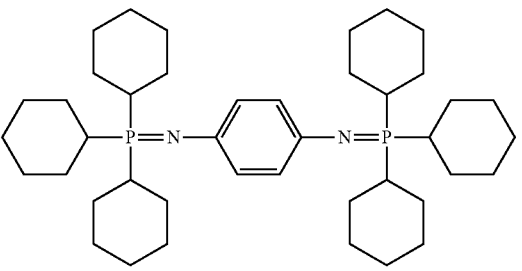 [SMILES: c1cc(N=P(C2CCCCC2)(C2CCCCC2)C2CCCCC2)ccc1N=P(C1CCCCC1)(C1CCCCC1)C1CCCCC1] | 28 |
| 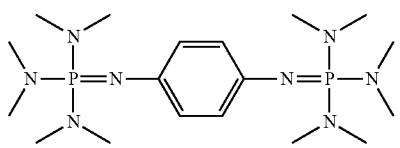 | 29 |

-continued

| compound | number |
|---|---|
| (structure: 1,5-bis(triphenylphosphinimine)-naphthalene) | 30 |
| (structure: 1,4-bis(diphenylphosphinimine-methyl)-benzene type) | 31 |

In the following, further details of some exemplary compounds according to Formula 1 are provided.

Compound 1:
1,4-bis(triphenylphosphinimine)-benzene 12.3 g (37.0 mmol) triphenylphosphine dichloride were dissolved in 80 ml benzene. 10 ml triethylamine and 2.0 g (18.5 mmol) 1,4-phenylene diamine were added and the mixture was heated for 2 days under reflux. After cooling, the suspension was filtered and the residue was washed first with diluted sodium hydroxide solution and then with ethanol/water. 9.20 g (14.6 mmol; 79%) yellow solid was obtained after drying in vacuum. The product was purified by gradient sublimation for analytical characterisation.

Melting point (DSC): 272° C.
CV (DCM): −0.40 V vs. Fc (rev)

Compound 2:
1,2-bis(triphenylphosphinimine)-benzene 10.0 g (30.0 mmol) triphenylphosphine dichloride was dissolved in 100 ml toluene. 8.5 ml triethylamine and 1.62 g (15.0 mmol) 1,2-phenylene diamine were added and the mixture was heated for 2 days at 95° C. After cooling, the suspension was filtered and the residue was washed with toluene. The residue was suspended in 2 M sodium hydroxide solution and stirred for 5 minutes at 45° C. 4.73 g (7.5 mmol; 50%) bright yellow solid were obtained after filtration and drying in vacuo. The product was purified by gradient sublimation for analytical characterisation.

Melting point (DSC): 257° C.
CV (DCM): −0.29 V vs. Fc

Compound 3:
1,4-bis(triphenylphosphinimine)-2-methoxy-benzene

1. Step: Reduction of 2-methoxy-4-nitroaniline 3.0 g (17.8 mmol) of 2-methoxy-4-nitroaniline and 0.8 g palladium on charcoal (10%) were added to 100 ml tetrahydrofurane. 8.7 ml (114.0 mmol) hydrazine monohydrate in 40 ml tetrahydrofuran were cautiously added and the reaction mixture was stirred at 90° C. for 3 hours. After cooling, the suspension was filtered and washed with tetrahydrofurane. The mother liquor was evaporated under reduced pressure to yield a gray residue. 2.44 g (17.7 mmol, 99%) product was stored under argon and used without further purification.

2. Step:
1,4-bis(triphenylphosphinimine)-2-methoxy-benzene 3.71 g (11.2 mmol) triphenylphosphine dichloride was dissolved in 50 ml toluene. A suspension of 3.1 ml (22.3 mmol) triethylamine and 0.77 g (5.6 mmol) 2-methoxy-1,4-phenylene diamine in 50 ml toluene was added and the mixture was heated for 2 days at 95° C. After cooling, the suspension was filtered, the residue washed with toluene, suspended in a 2 M sodium hydroxide solution, stirred for 5 minutes at 45° C., filtered and washed with water. 1.96 g (3.0 mmol; 53%) brown solid was obtained after filtration and drying in vacuum.

Melting point (DSC): 206° C.
CV (DCM): −0.45 V vs. Fc (rev)

Compound 4:
1,4-bis(tritolylphosphinimine)-benzene

1. Step: Preparation of
tris(4-methylphenyl)phosphine dichloride 11.70 g (49.3 mmol) hexachloroethane was added to a suspension of 15.0 g (49.3 mmol) tris(4-methylphenyl)phosphine in 80 ml acetonitrile under argon atmosphere. The mixture was stirred for 17 hours at 95° C. After cooling, the solvent was removed under reduced pressure and the residue washed with toluene and hexane. 9.83 g (26.2 mmol; 53%) white solid were obtained after drying in high vacuum. The compound was used in the next transformation without further purification.

2. Step: 1,4-bis(tritoluylphosphinimine)-benzene

A solution of 5.8 ml (41.6 mmol) triethylamine in 10 ml dry toluene was added under argon at 5° C. atmosphere to a mixture of 7.81 g (20.8 mmol) tris(4-methylphenyl)phosphine dichloridel in 80 ml dry toluene. 1.12 g (10.4 mmol) 1,4-phenylene diamine was added. The mixture was stirred at 110° C. for 1 hour. The yellow precipitate was filtered and washed with toluene and hexane. The dried crude product was suspended in 2 M sodium hydroxide solution and stirred for 5 minutes at 45° C. 5.43 g (7.6 mmol; 73%) bright yellow solid was obtained after filtration, washing with water and drying in vacuo. The product was purified by gradient sublimation for analytical characterisation.
Melting point (DSC): 267° C.
CV (DCM): -0.46 V vs. Fc (rev)

Compound 5:
1,4-bis(tritoluylphosphinimine)-2-methoxy-benzene

1. Step: Preparation of Tritoluylphosphine
Dichloride

See above

2. Step: Reduction of 2-methoxy-4-nitroaniline

See above

3. Step:
1,4-bis(tritoluylphosphinimine)-2-methoxy-benzene 2.0 g (5.3 mmol) tritoluylphosphine dichloride was dissolved in 10 ml toluene under argon. A suspension of 1.5 ml (10.7 mmol) triethylamine and 0.37 g (2.7 mmol) 2-methoxy-1,4-phenylene diamine in 15 ml toluene was added and the mixture was heated 18 hours at 90 ° C. After cooling, the suspension was filtered, the residue washed with toluene,suspended in a 2 molar sodium hydroxide solution and stirred for 5 minutes at 45° C., filtered and washed with water. 0.43 g (0.6 mmol; 22%) yellow solid was obtained after filtration and drying in vacuo.
Melting point (DSC): 239 ° C.
CV (DCM): -0.51 V vs. Fc.

Compound 7:
1,2,4,5-tetra(triphenylphosphinimine)-benzene 4.9 ml (35.2 mmol) triethylamine and 0.50 g (1.8 mmol) tetraaminobenzene tetrahydrochloride were suspended in 20 ml acetonitrile. 2.93 g (8.8 mmol) triphenylphosphine dichloride were dissolved in 15 ml acetonitrile and added to the suspension at 0° C. The mixture was stirred at room temperature for 18 hours. The precipitate was filtered off, suspended in 2 molar sodium hydroxide solution and stirred for 5 minutes at 45° C. 0.74 g (0.6 mmol; 35%) red brown solid was obtained after filtration and drying in vacuo.
Melting point (DSC): 283° C.
CV (DCM)=-1.02 V vs. Fc (rev.)

Compound 8: Tris(4-triphenylphospinimine phenyl)
amine 1.72 g (5.4 mmol) triphenylphosphine dichloride was dissolved in 8 ml dichloromethane under argon atmosphere. 1.8 ml (12.9 mmol) triethylamine in 2 ml dichloromethane was slowly added to the solution. 0.50 g (1.7 mmol) tris(4-aminophenyl)amine was added and the mixture was stirred at room temperature for 4 days. The reaction was diluted with dichloromethane and extracted with water. The organic phase was dried and the solvent removed under reduce pressure. The residue was suspended in 2 molar sodium hydroxide solution and stirred for 5 minutes at 45° C. 1.50 g (1.4 mmol; 82%) solid was obtained after filtration and drying in vacuo.
Melting point (DSC): 277° C.
CV (DMF): -0.39 V vs. Fc.

Compound 9: Tris(4-tritoluylphospinimine phenyl)
amine

1. Step: Preparation of Tritoluylphosphine
Dichloride

See above

2. Sep: tris(4-tritoluylphospinimine phenyl) amine

A solution of 3.8 ml (27.4 mmol) triethylamine in 10 ml dry toluene was added under argon atmosphere at 5° C. to a 3.82 g (10.2 mmol) tris(4-methylphenyl)phosphine dichloride dissolved in 40 ml toluene. 1.0 g (3.4 mmol) tris(4-aminophenyl)amine was added. The mixture was stirred at 110° C. for 1 hour. The precipitate was filtered and washed with toluene and hexane. The dried crude product was suspended in a 2 molar sodium hydroxide solution and stirred for 5 minutes at 45° C. 3.06 g (2.6 mmol; 75%) pale yellow solid was obtained after filtration, washing with water and drying in vacuo.

Compound 11: 4,4'-bis(triphenylphosphinimine)-1,
1'-biphenyl 4.15 g (12.5 mmol) triphenylphosphine dichloride was dissolved in 30 ml benzene. 3.4 ml triethylamine and 1.15 g (6.3 mmol) benzidine were added. The mixture was stirred under reflux for 3 hours. After cooling, the suspension was filtered and the yellow residue was washed first with diluted sodium hydroxide solution and then with ethanol/water. 3.20 g (4.7 mmol; 73%) yellow solid was obtained after drying in vacuo. The product was purified by gradient sublimation for analytical characterisation.
Melting point (DSC): 283° C.
CV (DCM): 0.0 V vs. Fc (rev.)

Compound 18:
4,4"-bis(triphenylphosphinimine)-p-terphenyl 2.50 g (7.5 mmol) triphenylphosphine dichloride was dissolved in 50 ml toluene. 2.9 ml triethylamine and 0.88 g (3.4 mmol) 4,4"-diamino-p-terphenyl were added and the mixture was heated for 2 days at 95° C. After cooling, the suspension was filtered and the residue was washed first with diluted sodium hydroxide solution and then with water and acetonitrile. 2.06 g (2.6 mmol; 78%) pale-yellow solid was obtained after drying in vacuum. The product was purified by gradient sublimation for analytical characterisation.

Melting point (DSC): 322° C.
CV (DCM): 0.22 V vs. Fc (rev)

Compound 19: N4,N4"-bis(tri-p-tolylphosphoranylidene)-[1,1':4',1"-terphenyl]-4,4"-diamine 1. Step: Preparation of Tritolylphosphine Dichloride 11.7 g ((49.3 mmol) hexachloroethane was added to a suspension of 15.0 g (49.3 mmol) tris(4-methylphenyl)phosphine in 80 ml acetonitrile under argon atmosphere. The mixture was stirred for 17 hours at 95° C. After cooling, 200 ml dry toluene were added and 50 ml acetonitrile removed under reduced pressure. The precipitate was filtered and washed with 50 ml dry toluene and 50 ml dry hexane. 9.83 g (53%) white solid was obtained after drying in high vacuum.

2. Step Preparation of N4,N4"-bis(tri-p-tolylphosphoranylidene)-[1,1':4',1"-terphenyl]-4,4"-diamine 1.69 g (4.5 mmol) in 3.3 ml dichloromethane was added to a solution of 0.52 g (2 mmol) tritolylphosphine dichloride in 5 ml toluene. After adding 1 g (10 mmol) triethylamine, the mixture was stirred at reflux for 3 hours. The precipitate was filtered, dried, suspended in 2 M sodium hydroxide solution and stirred for 5 minutes at 45° C. 0.93 g (1.1 mmol; 55%) brown solid was obtained after filtration, washing with water and drying in vacuo. The product was purified by gradient sublimation for analytical characterisation.

Melting point: 314° C.
CV (DCM): 0.18 V vs. Fc

Compound 20: N4,N4"-bis(tris(4-methoxyphenyl)phosphoranylidene)-[1,1':4',1"-terphenyl]-4,4"-diamine 1. Step: Preparation of 4,4"-diazido-1,1':4',1"-terphenyl 0.63 g (9.3 mmol) sodium nitrite in 5 ml water and 0.56 g (9.3 mmol) urea in 5 ml water were added to a mixture of 1.2 g (4.5 mmol) [1,1':4',1"-terphenyl]-4,4"-diamine, 7.5 ml acetic acid and 3.3 ml sulphuric acid at 0° C. After stirring for 1 hour, 0.64 g (9.8 mmol) sodium azide in 5 ml water was added slowly. The mixture was stirred 3 hours at room temperature and poured on ice. The precipitate was filtrated, washed with water and dried in vacuo. The 1.3 g (4.2 mmol, 93%) brown solid was used without further purification.

2. Step: N4,N4"-bis(tris(4-methoxyphenyl)phosphoranylidene)-[1,1':4',1"-terphenyl]-4,4"-diamine To a solution of 0.66 g (2.1 mmol) 4,4"-diazido-1,1':4',1"-terphenyl in 15 ml toluene, 1.48 g (4.2 mmol) tris(4-methoxyphenyl)phosphine in 5 ml toluene was added under argon atmosphere. After 18 hours stirring at room temperature, the solvent was distilled off and the residue washed with toluene. 1.70 g (1.8 mmol) yellow powder was obtained after drying in vacuo.

Melting point: 328° C.

Compound 28: N1,N4-bis(tricyclohexylphosphoranylidene)benzene-1,4-diamine 8.1 g ((34.2 mmol) hexachloroethane was added to a suspension of 9.6 g (34.2 mmol) tricyclohexylphosphine in 60 ml acetonitrile under argon atmosphere. The mixture was stirred for 16 hours at 95° C. After cooling to room temperature, a solution of 1.7 g (15.5 mmol) para-phenylene diamine and 11.5 ml (77.5 mmol) 2,3,4,6,7,8,9,10-octahydropyrimido[1,2-a]azepine in 25 ml acetonitrile was added. The mixture was stirred at 95° C. for 16 hours and allowed to cool to room temperature. The precipitate was filtered, dried, suspended in 2 M sodium hydroxide solution and stirred for 5 minutes at 45° C. 5 g (7.5 mmol; 49%) brown solid was obtained after filtration, washing with water and drying in vacuo. The product was purified by gradient sublimation for analytical characterisation.

Melting point: 277° C.
CV (THF): −0.07 V vs. Fc

Compound 29: N1,N4-bis[tris(dimethylamino)phosphoranylidene]benzene-1,4-diamine 14.5 g ((61.0 mmol) hexachloroethane was added to a suspension of 10.0 g (61.0 mmol) tris(dimethylamino)phosphine in 75 ml acetonitrile under argon atmosphere. The mixture was stirred for 16 hours at 100° C. After cooling to room temperature, a solution of 3 g (27.7 mmol) para-phenylene diamine and 20.6 ml (138.5 mmol) 2,3,4,6,7,8,9,10-octahydropyrimido[1, 2-a]azepine (1,8-diazobicyclo[5,4,0] undec-7-ene) in 15 ml acetonitrile was added. The mixture was stirred at 100° C. for 16 hours and allowed to cool to room temperature. The solvent was distilled off up to 20 ml, the precipitate was filtrated, dried, suspended in 2 M sodium hydroxide solution and stirred for 5 minutes at 45° C. Extraction with toluene and washing with ethylacetate and drying in vacuo gave 1.2 g (2.8 mmol; 10%) brown solid. The product was purified by gradient sublimation for analytical characterisation.

Melting point: 127° C.
CV (DCM): −0.61 V vs. Fc

Compound 30: N1,N5-bis(triphenylphosphoranylidene)naphthalene-1,5-diamine 4.17 g (12.5 mmol) triphenylphosphine dichloride was dissolved in 30 ml benzene. 3.4 ml triethylamine and 1.0 g (6.25 mmol) naphthalene-1,5-diamine were added and the mixture was heated for 3 days at 80° C. After cooling, the suspension was filtered, the residue suspended in 2 M sodium hydroxide solution and stirred for 5 minutes at 45° C. 2.18 g (3.21 mmol; 51%) yellow solid was obtained after filtration and drying in vacuo. The product was purified by gradient sublimation for analytical characterisation.

Melting point: 257° C.
CV (DCM): 0.26 V vs. Fc

Compound 31: N1,N4-bis(methyldiphenylphosphoranylidene)benzene-1,4-diamine 4.7 g ((20 mmol) hexachloroethane was added to a suspension of 4 g (20 mmol) methyldiphenylphosphine in 25 ml acetonitrile under argon atmosphere. The mixture was stirred for 2.5 hours at 95° C. After cooling to room temperature, a solution of 0.98 g (9.1 mmol) para-phenylene diamine and 6.3 ml (45.5 mmol) 2,3,4,6,7,8,9,10-octahydropyrimido[1,2-a]azepine in 10 ml acetonitrile was added. The mixture was stirred at 95° C. for 16 hours and allowed to cool to room temperature. The precipitate was filtered, dried, suspended in 2 M sodium hydroxide solution and stirred for 5 minutes at 45° C. 1.2 g (2.4 mmol; 26%) brown solid was obtained after filtration, washing with water and drying in vacuo. The product was purified by gradient sublimation for analytical characterisation.

Melting point: 225° C.

CV (DCM): −0.23 V vs. Fc

The compounds proved to be effectively able to n-dope typical ETMs for OPVs. For example, C60 doped with 10 mol % of compound 1 showed a conductivity of 1.3 S/cm. C60 doped with 10 mol % of compound 4 showed a conductivity of 4.6 S/cm. C60 doped with 10 mol % of compound 2 showed a conductivity of 2.1E-2 S/cm. C60 doped with 10 mol % of compound 28 showed a conductivity of 2.1E-2 S/cm. C60 doped with 10 mol % of compound 29 showed a conductivity of 0.35 S/cm. C60 was used as a standard reference and it is clear that other electron transport materials with similar electronic transport properties can also be doped. For example, 2,2',2''-(5H-diindeno[1,2-a:1',2'-c]fluorene-5,10,15-triylidene)trimalononitrile (ET1) doped with 10 mol. % of compounds 28 and 29, respectively, showed each a conductivity of more than 1E-4 S/cm which is sufficient, for instance, for OPV applications.

Device 1: A pn junction device was used to benchmark the new dopants according to Formula 1 with the strong donor Tetrakis (1,3,4,6,7,8-Hexahydro-2H-pyrimido [1,2-a] pyrimi-dinato) ditungsten (II) (W(hpp)4). The pn-junction device was made on a glass substrate using ITO as anode, a 50 nm p-doped HTL (hole transport layer), a 50 nm C60 layer doped with one of the new dopants according to Formula 1 as ETL (electron transport layer), and an Al cathode. The voltage necessary for a current density of 5 mA/cm$^2$ was 0.09 V for compound 1, 0.12 V for compound 2, and 0.03 V for compound 4. These values are surprisingly good given the much lower donating strength than W(hpp)4 (HOMO<<−1.0 V vs Fc), which in a comparative example required a voltage of 0.01 V for the same current density.

Device 2 (comparative): A state of the art organic solar cell was fabricated with the following procedure. A patterned glass substrate coated with ITO was cleaned with standard procedure. The substrate was loaded into the vacuum trough a glove box with nitrogen. In vacuum, the organic layers were deposited with conventional VTE (vacuum thermal evaporation). First a 40 nm thick 15 .% (molar) p-doped N4,N4,N4'',N4''-tetra([1,1'-biphenyl]-4-yl)-[1,1':4',1''-terphenyl]-4,4''-diamine (HT1) layer was deposited through a shadow mask over the ITO. A 10 nm undoped Boron subphthalocyanine chloride (SubPc) layer was deposited over the doped HT1. A 25 nm undoped C60 layer followed. A 15 nm thick C60 layer doped (10 wt.%) with the strong n-dopant W(hpp)4 was deposited on top of the undoped C60 layer. An Al cathode was deposited on top. Under simulated solar spectra, the device showed the following parameters: Voc=1.06 V, Jsc=4.83 mA/cm$^2$, FF =52.5%, efficiency of 2.7%.

Figure 3:
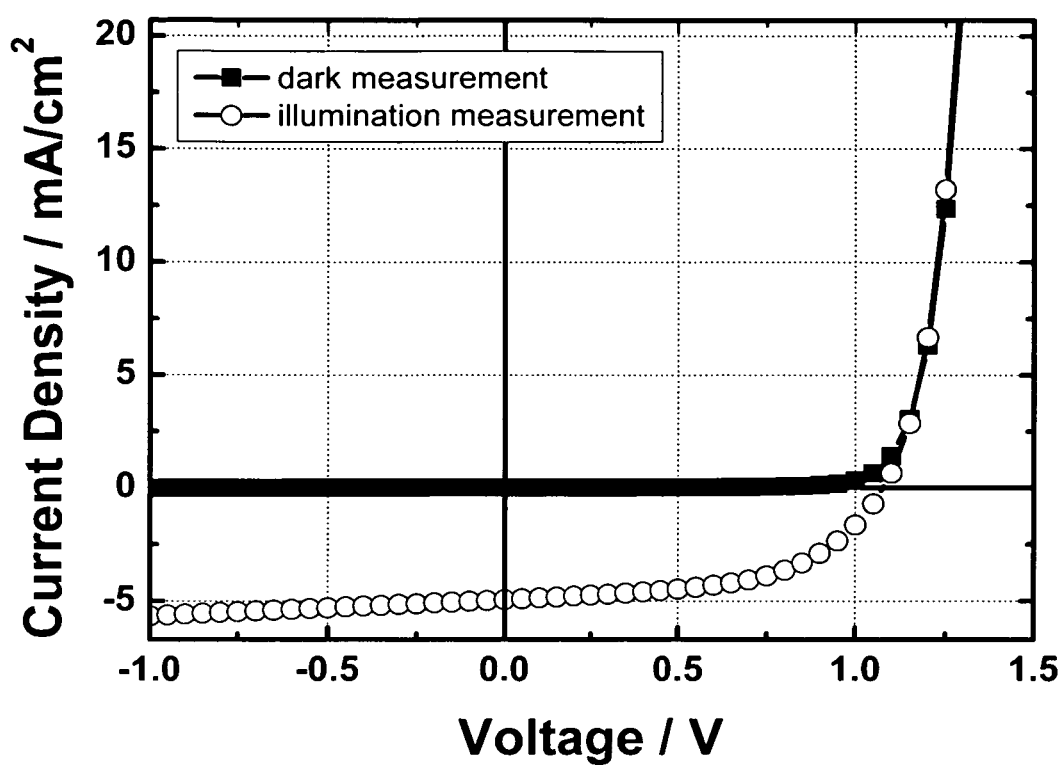
FIG. 3 shows the I×V (current versus voltage) curves of a solar cell with and without illumination.

Device 3: An organic solar cell can be made with the same layer structure as device 2 except that compound 4 was used instead of W(hpp)4. Under identical conditions, the device typically shows increased performance with a short circuit current of 4.93 mA/cm$^2$, a FF of 54.9% and an open circuit voltage of 1.08 V with an overall power efficiency of 2.91%. The I×V curves of the device with and without illumination are shown in FIG. 3.

Tandem organic solar cells comprising the new compound according to Formula 1 as dopants show higher power conversion efficiency than a comparative device, which were identical except for the n-dopant (W(hpp)4). Power conversion efficiency up to 3.9% could be achieved, while the best comparative tandem solar cell had 3.7%. A replacement of C60 by ET1 in the 5 nm thick ETL of the pn junction, further improved the efficiency to 4.2%. That shows that the use of the new compound according to Formula 1 as dopant in electron transport layers which are connected to or part of a pn junction further improves organic electronic devices, especially organic solar cells.

The features of the invention disclosed in the above specification, the claims and the drawing may be important individually as well as in any combination for the implementation of the invention in its various embodiments.

The invention claimed is:

1. An electronic device comprising an n-dopant according to formula 1:

A-B       (1), wherein

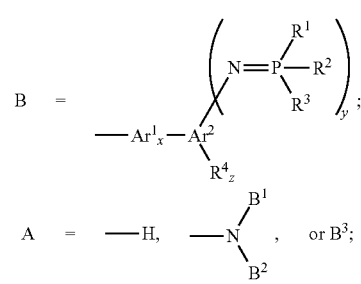

and wherein

Ar$^1$ is a C6-C18 arylene,

Ar$^2$ is a C6-C18 arene skeleton, and R$^4$ is selected independently from electron donating groups, B$^1$ and B$^2$ are independently selected from B or Ar$^2$, B$^3$ is independently selected from the same group as B, R$^1$, R$^2$, and R$^3$ are independently selected from alkyl, arylalkyl, cycloalkyl, aryl, or dialkylamino, x is selected from 0, 1, 2 or 3, wherein when x>1 each Ar$^1$ may be different, y is a non-zero integer up to the overall count of valence sites on the arene skeleton, and z is a integer from zero up to the overall count of valence sites on the arene skeleton minus y.

2. The electronic device according to claim 1, wherein any of R$^1$, R$^2$, and R$^3$ is independently selected from straight or branched, saturated or unsaturated C1-C24 alkyl, saturated or unsaturated C3-C24 cycloalkyl or alkyl comprising at least one cyclic structure, C6-C24 aryl, wherein the overall count of carbon atoms includes also any possible substitution by a single substituent or more substituents selected from saturated or unsaturated, straight or branched alkyl or cycloalkyl, aryl, arylalkyl or alkylaryl groups and within this substitution up to three alkyl groups can be attached to the arene core by an ether linkage or up to six alkyl groups can be attached through a disubstituted nitrogen atom, C7-C25 arylalkyl, wherein the overall C atom count includes also a possible substitution on the arene ring or rings and within this substitution up to three alkyl groups can be attached to the arene ring or rings through an ether linkage or up to six alkyl groups through a disubstituted nitrogen atom, C2-C24 dialkylamino, wherein the alkyl groups may be the same or different, straight or branched, may include also alicyclic or aromatic structures or be unsaturated with a provision that the carbon atom bearing a double or triple bond is not adjacent to nitrogen, the two alkyls in the dialkylamino group may be so linked that they form a cycle comprising the nitrogen atom and up to four ether linkages can be included between methylene groups of the dialkylamino group, and with a provision that in any case the nitrogen and/or oxygen atoms are separated by at least two carbon atoms, or two groups selected from $R^1$-$R^3$ may be linked so that they form a cyclic structure including a phosphorus atom.

3. The electronic device according to claim 2, wherein any of $R^1$, $R^2$, and $R^3$ is independently selected from C1-C4 alkyl, C3-C10 cycloalkyl, C7-C10 arylalkyl, C6-C14 aryl, or C2-C12 dialkylamino.

4. The electronic device according to claim 1, wherein $Ar^2$ is a benzene or naphthalene skeleton,
$Ar^1$ is phenylene, or x is 0,
y is selected from 1, 2, 3 or 4 if $Ar^2$ is benzene, or from 1, 2, 3, 4, 5, or 6 if $Ar^2$ is naphthalene, and
z is selected from 0 or 1 if $Ar^2$ is benzene, or from 0, 1, or 2 if $Ar^2$ is naphthalene.

5. The electronic device according to claim 4, wherein $Ar^2$ is a benzene skeleton, and
$Ar^1$ is 1,4-phenylene or x is 0.

6. The electronic device according to claim 1, wherein each of $R^1$-$R^3$ is independently selected from methyl, isopropyl, tert-butyl, cyclohexyl, phenyl, tolyl, xylyl, mesityl, naphthyl, anthryl, phenanthryl, 1,1'-biphenyl-yl, 1,3-diisopropylphenyl, benzyl, 4-methoxybenzyl, or dimethylamino.

7. The electronic device according to claim 1, wherein the device has a layered structure comprising several layers.

8. The electronic device according to claim 7, wherein a layer comprising the n-dopant of Formula 1 is an electron transport layer.

9. The electronic device according to claim 7, wherein a layer comprising the n-dopant of Formula 1 has a thickness of less than 5 nm.

10. The electronic device according to claim 7, wherein the layer comprising the n-dopant of Formula 1 is in direct contact to an electrode.

11. The electronic device according to claim 7, wherein a layer comprising the n-dopant of Formula 1 is in direct contact to an electron transport layer.

12. The electronic device according to claim 7, wherein a layer comprising the n-dopant of Formula 1 is part of a connecting unit, the connecting unit comprising a pn-junction connecting a first light absorbing unit to a second light absorbing unit in a tandem device or a multiple stacked device.

13. The electronic device according to claim 1, wherein the device is a solar cell.

14. The electronic device according to claim 1, wherein each $R^4$ is independently selected from alkyl, alkoxy, aryl, or aryloxy having an overall count of carbon atoms in the range of C1-C22.

15. The electronic device according to claim 14, wherein each $R^4$ is independently selected from methyl, methoxy, ethyl, ethoxy, propyl, propoxy, isopropyl, isopropoxy, butyl, butoxy, tert-butyl, tert.-butoxy, cyclohexyl, benzyl, or benzyloxy.

16. The electronic device according to claim 2, wherein up to four ether linkages can be included within any of the C3-C24 alkyl or cycloalkyl structures with a provision that oxygen atoms are in any case separated by at least two carbon atoms.

17. The electronic device according to claim 10, wherein the electrode is a cathode.

18. The electronic device according to claim 1, wherein $Ar^1$ is a polycyclic C8-C18 arylene that is substituted by one or more C1-C10-alkyl or C3-C10-cycloalkyl groups.

* * * * *